United States Patent
Govari et al.

(10) Patent No.: US 8,641,708 B2
(45) Date of Patent: Feb. 4, 2014

(54) MEASURING WEAK SIGNALS OVER ABLATION LINES

(75) Inventors: Assaf Govari, Haifa (IL); Yaron Ephrath, Karkur (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 962 days.

(21) Appl. No.: 12/648,327

(22) Filed: Dec. 29, 2009

(65) Prior Publication Data

US 2011/0160716 A1 Jun. 30, 2011

(51) Int. Cl.
*A61B 18/18* (2006.01)
(52) U.S. Cl.
USPC .............................. 606/41; 606/32
(58) Field of Classification Search
USPC ............................... 606/32–34, 41
See application file for complete search history.

(56) References Cited

U.S. PATENT DOCUMENTS

| | | | |
|---|---|---|---|
| 4,411,266 A * | 10/1983 | Cosman | 606/49 |
| 4,966,597 A * | 10/1990 | Cosman | 606/50 |
| 6,190,379 B1 | 2/2001 | Heuser et al. | |
| 6,371,926 B1 * | 4/2002 | Thorson et al. | 600/549 |
| 6,425,894 B1 * | 7/2002 | Brucker et al. | 606/41 |
| 6,692,492 B2 * | 2/2004 | Simpson et al. | 606/41 |
| 7,306,596 B2 * | 12/2007 | Hillier et al. | 606/41 |
| 7,318,822 B2 * | 1/2008 | Darmos et al. | 606/31 |
| 7,569,052 B2 | 8/2009 | Phan et al. | |
| 7,766,905 B2 * | 8/2010 | Paterson et al. | 606/34 |
| 2008/0119846 A1 | 5/2008 | Rioux | |
| 2008/0167646 A1 * | 7/2008 | Godara et al. | 606/41 |
| 2008/0294144 A1 | 11/2008 | Leo et al. | |
| 2009/0306641 A1 * | 12/2009 | Govari et al. | 606/33 |
| 2011/0270247 A1 * | 11/2011 | Sherman | 606/41 |

FOREIGN PATENT DOCUMENTS

| | | |
|---|---|---|
| EP | 2 008 603 A1 | 12/2008 |
| WO | WO 98/19595 A2 | 5/1998 |

OTHER PUBLICATIONS

Extended European Search Report dated Mar. 13, 2012 from related European Application No. 11191800.9.

* cited by examiner

*Primary Examiner* — Linda Dvorak
*Assistant Examiner* — Jocelyn D Ram
(74) *Attorney, Agent, or Firm* — Louis J. Cappezzuto, Esq.

(57) ABSTRACT

A medical probe, including an ablation electrode and a first conductor connected to the ablation electrode. The first conductor is configured to convey ablation energy to the ablation electrode. The probe also includes a second conductor which is connected at a junction to the first conductor so as to form a thermocouple at the junction.

9 Claims, 3 Drawing Sheets

MEASURING WEAK SIGNALS OVER ABLATION LINES

FIELD OF THE INVENTION

The present invention relates generally to medical probes, and specifically to improving the efficiency of operation of the probes.

BACKGROUND OF THE INVENTION

Medical catheters typically have as small a diameter as possible. However, since the catheter typically contains a number of elements, such as an ablation electrode, a strain gauge, position sensors, a temperature-measuring element, together with their associated signal transmitting conductors, there is a practical lower limit to the catheter diameter. It would be advantageous to reduce this lower limit.

A brief description of prior art regarding some of the above-mentioned elements follows.

U.S. Pat. No. 6,190,379, to Heuser, et al., whose disclosure is incorporated herein by reference, describes a system for treating a blockage in a bodily fluid passageway. The system includes a catheter and a controller for generating radio frequency energy along a pair of output lines, and includes a thermocouple.

U.S. Pat. No. 7,569,052, to Phan, et al., whose disclosure is incorporated herein by reference, describes a medical probe having an ablative element and an optional temperature sensing element.

United States Patent Application Publication 20080294144, to Leo, et al., whose disclosure is incorporated herein by reference, describes a touch sensing catheter having a strain sensor assembly. The catheter includes an ablation head assembly.

United States Patent Application Publication 20080119846, to Rioux, whose disclosure is incorporated herein by reference, describes a percutaneous probe comprising a sensor capable of sensing physiological information, such as the impedance, temperature, or pressure, of tissue adjacent to a tip electrode of the probe.

The description above is presented as a general overview of related art in this field and should not be construed as an admission that any of the information it contains constitutes prior art against the present patent application.

SUMMARY OF THE INVENTION

An embodiment of the present invention provides a medical probe, including:

an ablation electrode;

a first conductor connected to the ablation electrode and configured to convey ablation energy thereto; and a second conductor connected at a junction to the first conductor so as to form a thermocouple at the junction.

Typically, the junction is located to contact the ablation electrode, so as to be galvanically connected thereto. Alternatively, the junction is located so as not to contact the ablation electrode, while the junction is galvanically connected to the ablation electrode.

The first and the second conductors may be configured to convey from the junction a low-frequency voltage generated by the junction.

There is further provided, according to an embodiment of the present invention, a medical apparatus, including:

a probe including an ablation electrode;

a first conductor connected to the ablation electrode and configured to convey ablation energy thereto;

a second conductor connected at a junction to the first conductor so as to form a thermocouple at the junction;

a radiofrequency generator coupled to the first conductor and configured to generate the ablation energy; and a processor coupled to the first and second conductors so as to measure a temperature of tissue to which the ablation energy is applied.

Typically, the medical apparatus includes a mixer coupled to the first and second conductors so as to receive a voltage therefrom.

The mixer may be configured to receive radiofrequency energy from the radiofrequency generator as a local oscillation.

In one embodiment the mixer is configured to output a radiofrequency signal having a frequency determined by the radiofrequency generator. Typically, an amplitude of the radiofrequency signal is a function of the temperature of the tissue. Alternatively or additionally, an amplitude of the radiofrequency signal may be a function of the voltage from the first and second conductors.

There is further provided, according to an embodiment of the present invention, a medical apparatus, including:

a probe having distal and proximal ends and including an electrode at the distal end, which is configured to contact body tissue and is coupled by one or more conductors to the proximal end;

an energy source, which is configured to apply energy at a radiofrequency to the one or more conductors for application by the electrode to the body tissue;

an oscillator, which is configured to generate a local oscillation signal at the radiofrequency;

a mixer, which is coupled to receive an input signal from the one or more conductors and to mix the input signal with the local oscillation signal in order to generate an output signal having a signal component at the radiofrequency; and processing circuitry, which is configured to process the signal component so as to extract a value of a low-frequency signal carried by the one or more conductors.

Typically, the probe includes an ablation probe and the electrode in contact with the body tissue is configured to ablate the tissue.

Typically, the energy source includes an amplifier, and the oscillator is coupled to the amplifier so as provide the energy at the radiofrequency.

In a disclosed embodiment the signal component has an amplitude which is a function of the value of the low-frequency signal.

In a further disclosed embodiment the processing circuitry includes a converter which is configured to convert the signal component to a DC level corresponding to the value of the low-frequency signal.

There is further provided, according to an embodiment of the present invention, a method for providing a medical probe, including:

providing an ablation electrode;

connecting a first conductor to the ablation electrode;

configuring the first conductor to convey ablation energy to the ablation electrode; and connecting a second conductor at a junction to the first conductor so as to form a thermocouple at the junction.

There is further provided, according to an embodiment of the present invention, a method for providing a medical apparatus, including:

providing a probe including an ablation electrode;
connecting a first conductor to the ablation electrode;
configuring the first conductor to convey ablation energy to the ablation electrode;
connecting a second conductor at a junction to the first conductor so as to form a thermocouple at the junction;
coupling a radiofrequency generator to the first conductor and configuring the radiofrequency generator to generate the ablation energy; and
coupling a processor to the first and second conductors so as to measure a temperature of tissue to which the ablation energy is applied.

There is further provided, according to an embodiment of the present invention, a method for providing medical apparatus, including:
providing a probe having distal and proximal ends and including an electrode at the distal end;
configuring the probe to contact body tissue and to be coupled by one or more conductors to the proximal end;
applying energy from an energy source at a radiofrequency to the one or more conductors for application by the electrode to the body tissue;
generating with an oscillator a local oscillation signal at the radiofrequency;
coupling a mixer to receive an input signal from the one or more conductors and to mix the input signal with the local oscillation signal in order to generate an output signal having a signal component at the radiofrequency; and
configuring processing circuitry to process the signal component so as to extract a value of a low-frequency signal carried by the one or more conductors.

The present disclosure will be more fully understood from the following detailed description of the embodiments thereof, taken together with the drawings, in which:

DETAILED DESCRIPTION OF EMBODIMENTS

Overview

An embodiment of the present invention comprises a medical probe, typically a catheter, which at its distal end has an ablation electrode in proximity to a thermocouple. The thermocouple is formed from two dissimilar conductors which are connected at a junction, and the thermocouple outputs a low level low-frequency voltage, of the order of tens or hundreds of millivolts, which is proportional to the temperature of the distal end.

The ablation electrode requires high intensity radiofrequency (RF) energy, typically on the order of a hundred volts or more, in order to operate. In prior art catheters this RF energy is supplied from an RF generator to the electrode by an ablation conductor, separate from the thermocouple conductors. In order to accurately detect the thermocouple's low level voltage, the prior art catheters typically require isolation between the ablation conductor and the thermocouple conductors.

In complete contrast to the prior art systems, embodiments of the present invention have a common conductor for the ablation energy and the thermocouple. The other, non-common, conductor of the thermocouple consequently has an RF leakage component at the frequency of the RF generator. A mixer is coupled to the non-common thermocouple conductor, thus receiving the thermocouple low level voltage with the RF leakage component. To recover the low level voltage, the mixer receives a portion of RF energy from the RF generator, and uses this for local oscillation. The amplitude and phase of the local oscillation are adjusted to cancel the RF leakage component of the thermocouple, so that the mixer outputs an AC signal at the local oscillation frequency, with an amplitude proportional to the thermocouple voltage. A detector senses the amplitude to measure the temperature at the thermocouple junction.

In prior art systems, RF signals are demodulated by a mixer in order to extract the information that the signals carry. Embodiments of the invention take the opposite approach: The mixer modulates a low-frequency low level signal onto an RF carrier for purposes of detection. This approach reduces the need for filtering and may enhance the accuracy of detection.

Other embodiments of the present invention use the principles described herein to extract signals formed at the distal end of a probe, including low-frequency AC signals comprising DC signals, other than those from a thermocouple. Such signals include, but are not limited to, ECG signals and strain gauge signals. The use of a common conductor to convey high intensity RF signals together with other signals reduces the number of conductors that must pass through the probe, and therefore helps in reducing the diameter and increasing the flexibility of the probe.

System Description

Figure 1:
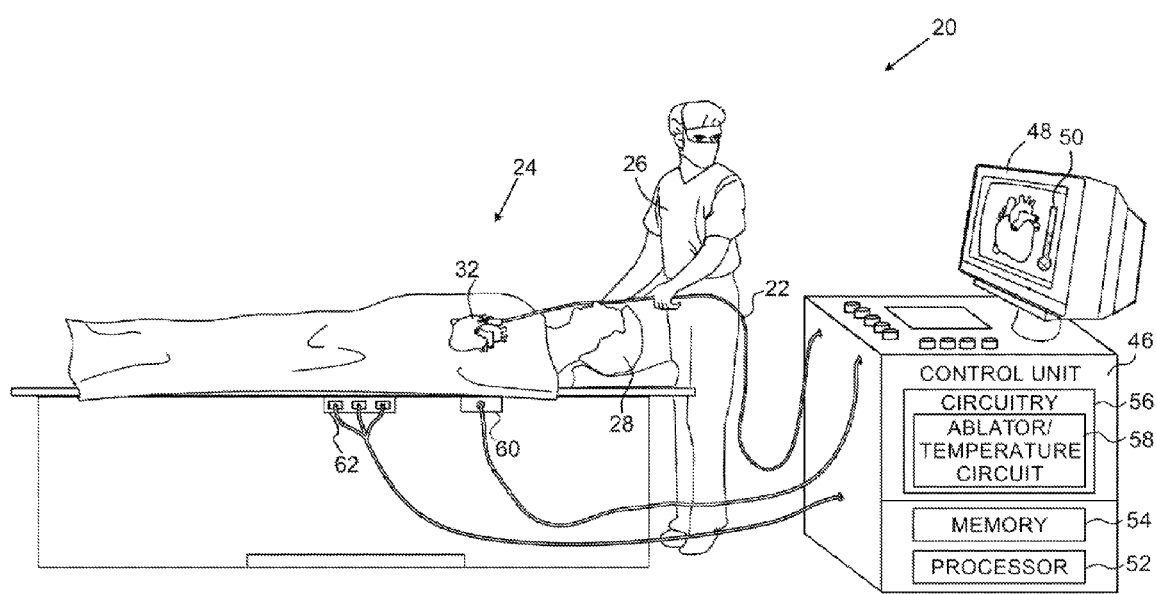
FIG. 1 is a schematic, pictorial illustration of a medical system comprising a probe, according to an embodiment of the present invention.
Figure 2:
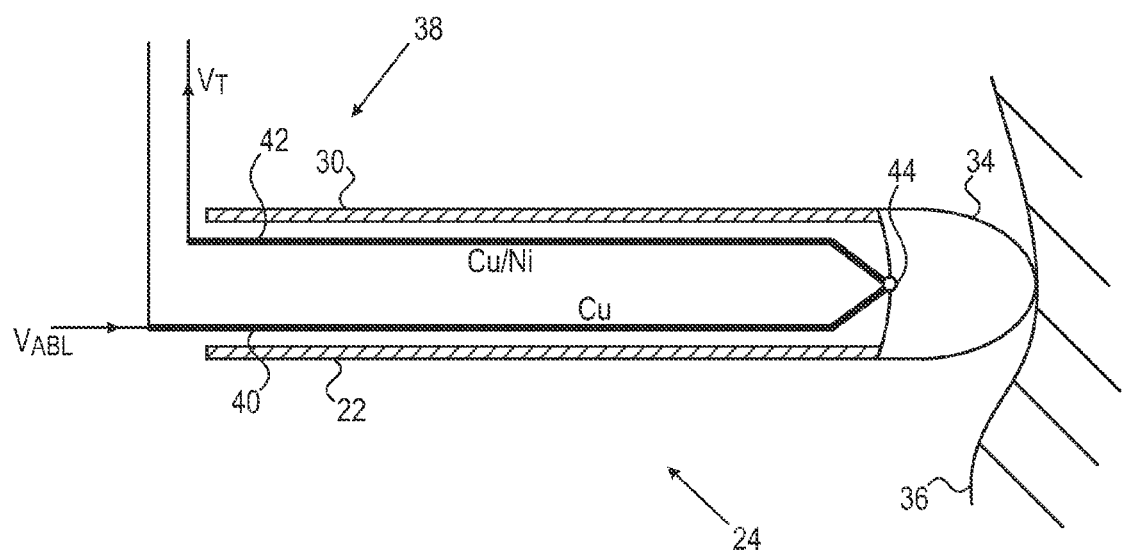
FIG. 2 is a schematic view inside a distal end of the probe, according to an embodiment of the present invention.

FIG. 1 is a schematic, pictorial illustration of a medical system 20 comprising a probe 22, and FIG. 2 is a schematic view inside a distal end 24 of the probe, according to respective embodiments of the present invention. Probe 22 is herein assumed, by way of example, to comprise a catheter. Catheter 22 is inserted by an operator 26 of the system into a patient 28 upon which a medical procedure is being performed.

FIG. 2 shows components of the catheter that are located at the distal end. For clarity, not all components located at distal end 24 are shown in the figure. Components that are typically present in the catheter, but which are not shown in the figure, typically include position and orientation sensing devices which allow operator 26 to track distal end 24.

Catheter 22 comprises a flexible insertion tube 30, which forms an outer sleeve of the catheter. By way of example, the catheter is assumed to be inserted into a chamber of a heart 32. (In the case of the heart, the catheter is typically inserted percutaneously through a blood vessel, such as the vena cava or the aorta.)

An ablation electrode 34 terminates tube 30 and is fixedly attached to the tube. The electrode is assumed to engage endocardial tissue 36, and on receipt of radiofrequency (RF) energy in the form of a high intensity oscillation, performs ablation on tissue 36. The RF energy transfers from electrode 34, via tissue 36 and the body of the patient, to a grounding electrode 60 which is typically conductively connected to the patient's skin.

A thermocouple 38 is located at distal end 24, within tube 30. The thermocouple comprises a first conductor 40, and a second conductor 42, the two conductors being connected galvanically at a junction 44. The two conductors are selected to be different, so that their junction 44 operates as a temperature sensing thermocouple junction. Typically the two conductors are selected from known components that have thermocouple voltage-temperature relations that are already known. By way of example, first conductor 40 is assumed to comprise copper, and second conductor 42 is assumed to comprise a copper-nickel alloy such as constantan. Junction 44 is also galvanically connected to ablation electrode 34. The galvanic connection may be implemented by locating the junction on a surface of, or within, electrode 34. Alternatively, the junction may be galvanically connected to the electrode, but may be located so that it does not contact the ablation electrode.

Operator 26 uses a control unit 46 to operate system 20 and probe 22. At its proximal end the probe is connected, together with internal elements of the probe such as conductors, to the control unit. Unit 46 comprises a graphic user interface (GUI) 48 upon which is presented information generated by the system, such as a temperature gauge 50 providing a temperature of junction 44, or a three-dimensional map of a region of tissue 36 being ablated by electrode 34.

The control unit also comprises a processor 52. The processor, under overall control of the system operator, uses software stored in a memory 54 for signal analysis, to control and operate hardware elements including circuitry 56 of system 20, and to perform other functions related to operation of the system. The software typically includes the thermocouple voltage-temperature relations referred to above, and the relations may be referred to by the processor in performing a calibration operation described below. The software may be downloaded to unit 46 in electronic form, over a network, for example, or it may, alternatively or additionally, be provided and/or stored on tangible media, such as magnetic, optical, or electronic memory.

Circuitry 56, inter alia, typically comprises elements that control magnetic field devices 62, typically transmitters or receivers, for the position and orientation sensing devices in the catheter referred to above. Circuitry 56 also comprises an ablator/temperature-measuring circuit 58, also referred to herein as ablator/temperature circuit 58, which supplies the RF ablation energy as an RF voltage $V_{ABL}$ to electrode 34, and which also receives and measures a temperature dependent voltage $V_T$ generated by junction 44. Voltage $V_T$ comprises a low-frequency voltage, typically varying from DC to approximately 1,000 Hz. Ablator/temperature circuit 58 is described in more detail with reference to FIG. 3.

Figure 3:
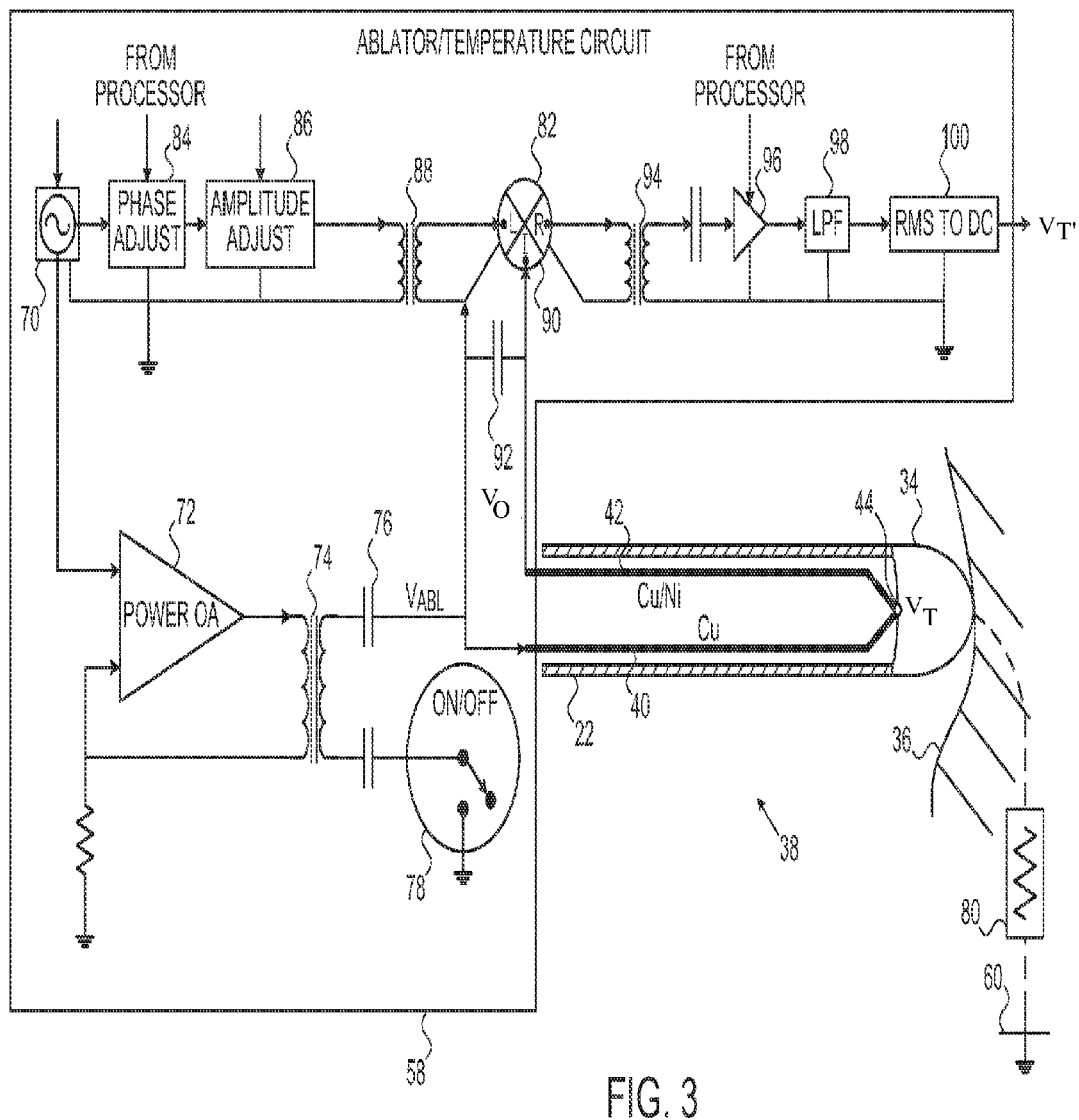
FIG. 3 is a schematic circuit diagram of an ablator/temperature-measuring circuit, according to an embodiment of the present invention.

FIG. 3 is a schematic circuit diagram of ablator/temperature-measuring circuit 58, according to an embodiment of the present invention. The diagram shows how the circuit is connected to thermocouple 38 and electrode 34 of catheter 22. Circuit 58 comprises an RF generator 70, typically a low power programmable waveform generator or a direct digital synthesis (DDS) device. A suitable RF generator is the AD 9833 produced by Analog Devices Corporation of Norwood, Mass. RF generator 70 is under overall control of processor 52, which adjusts the generator to output a sinusoidal waveform having a frequency between approximately 400 kHz and approximately 600 kHz. The generator is configured to provide two outputs for its RF energy.

A first output from generator 70 is used as an input to a power amplifier 72, typically a power operational amplifier such as the PA119CE produced by Cirrus Logic Corporation of Austin, Tex. Amplifier 72 is configured to amplify its low level input so as to output its RF power at a level of approximately 70 W. The output from the amplifier is transferred via a transformer 74, which adjusts a voltage level of the amplifier output to a level $V_{ABL}$ that is high enough to perform ablation. Voltage $V_{ABL}$ is delivered from the secondary coil of transformer 74, via an isolating capacitor 76, to first conductor 40 of the thermocouple, and from there to ablation electrode 34. Conductor 40 thus acts as a common conductor for the thermocouple and the ablation electrode.

A switch 78, connected via a capacitor to the secondary coil of transformer 74, operates to activate the supply of RF energy to the ablation electrode by providing a path to ground when closed. As shown in FIG. 3 by a broken line and a resistor 80, there is also a return to ground for the ablation energy, via the resistance of body tissue 36 and grounding electrode 60. Operator 26 controls the operation of switch 78 via control unit 46.

A second output from generator 70 is used to provide an input as a local oscillator to a mixer 82. The local oscillator input to the mixer is derived by adjusting the phase and amplitude of the second input in a phase adjust element 84 and an amplitude adjust element 86. Both elements are assumed to be implemented so that their respective values, phase shift and amplitude level, may be adjusted by processor 52. Phase element 84 may conveniently be implemented using an RC series circuit, with at least one of the R (resistance) or C (capacitance) variable, and one or more operational amplifiers; amplitude adjust element 86 may conveniently be implemented using variable and fixed resistances and one or more operational amplifiers. Both implementations will be familiar to those having ordinary skill in the art. These and other implementations of phase adjust element 84 and amplitude adjust element 86 known in the art are assumed to be within the scope of the present invention.

The adjusted second output is transferred, via an isolating transformer 88 which is typically a ferrite transformer, to mixer 82.

Mixer 82, which is typically a passive mixer such as the SRA-3 mixer produced by Mini-Circuits Corporation of Brooklyn, N.Y., has a "local" ground 90, which for the SRA-3 may comprise the case of the mixer. The secondary coil of transformer 88 is connected between local ground 90 and a local oscillator input terminal L of the mixer.

Mixer 82 receives a second input, which is connected between a terminal I of the mixer and the mixer's local ground. The second input is provided by connections from the two conductors of thermocouple 38. First conductor 40 of the thermocouple is connected to local ground 90, and second conductor 42 is connected to terminal I. Typically, a capacitor 92 is connected between the local ground and terminal I.

The mixer generates a resultant output between a terminal R and the local ground. The resultant output is connected to the primary coil of an isolating transformer 94, which is typically similar to transformer 88. The secondary terminals of transformer 94 are connected to the input of an instrumentation amplifier 96, typically a high accuracy instrumentation amplifier such as the INA101 produced by Texas Instruments Incorporated of Dallas, Tex. The gain of amplifier 96 may be set by processor 52.

The output of amplifier 96 is filtered of harmonics of the frequency generated by RF generator 70, herein referred to as the fundamental frequency, in a suitable filter 98. Filter 98 is typically a low pass filter having a cut-off below the second harmonic of the fundamental frequency, but may be a band pass filter only allowing transfer of the fundamental frequency.

Filter 98 provides its output to an RMS to DC converter 100. Converter 100 measures the root mean square (RMS) energy of the received input, and outputs a DC value corresponding the measured energy. RMS to DC converter 100 is typically highly linear; a suitable converter is the LTC1968 produced by Linear Technology Corporation of Milpitas, Calif. As explained below, the output DC voltage of converter 100, $V_T'$, is directly proportional to the voltage $V_T$ developed at junction 44. Typically, processor 52 receives output voltage $V_T'$, and uses it, for example, to provide a measurement of the temperature of junction 44 to operator 26, such as by operating temperature gauge 50 on GUI 48. Alternatively or additionally, output voltage $V_T'$ may be used for substantially any other purpose requiring a measure of the temperature of junction 44.

In operation of ablator/temperature circuit 58, because the RF voltage, $V_{ABL}$, supplied to electrode 34 is conveyed by one of the conductors of thermocouple 38 (in the example described above conductor 40) there is typically a relatively large leakage component of the RF energy at the output of the thermocouple. While capacitor 92 may reduce the size of the leakage component, it will not eliminate it.

The overall level output from the thermocouple may be written as:

$$V_O = V_T + LC(V_{ABL}) \quad (1)$$

where $V_O$ is the overall voltage output of the thermocouple,
$V_T$ is the voltage developed at junction 44, and
$LC(V_{ABL})$ is the leakage component of RF voltage $V_{ABL}$ developed in the thermocouple; $LC(V_{ABL})$ has the same frequency as $V_{ABL}$, but typically differs in both phase and amplitude.

The overall thermocouple voltage $V_o$ is input to terminal I of mixer 82.

As described below, the phase and amplitude of the RF signal to terminal L of the mixer are adjusted in a calibration operation so as to cancel the leakage component $LC(V_{ABL})$. Once the leakage component has been cancelled, the output of the mixer at terminal R is an AC signal, at the frequency of generator 70, with an amplitude proportional to $V_T$. The value of $V_T'$ (the output of converter 100) is also proportional to the amplitude, so that a relation between $V_T$ and $V_T'$ is:

$$V_T' = kV_T \quad (2)$$

where k is a constant.

Constant k is typically determined in the calibration operation.

As stated above, the phase and amplitude of the RF signal are adjusted to cancel the leakage component $LC(V_{ABL})$ in a calibration operation. A typical calibration operation comprises processor 52 adjusting phase adjust element 84 and amplitude adjust element 86 so as to minimize the circuit output voltage $V_T'$, the minimization effectively cancelling the effect on $V_T'$ of the leakage component. It will be appreciated that the calibration operation may be performed by the processor on a substantially automatic basis, and that it also may be performed while system 20 is being used during a medical procedure, or while the system is not being used for such a procedure. Typically, processor 52 may also operate the phase and amplitude adjust elements so as to counteract any fluctuations derived from generator 70.

Once the output voltage $V_T'$ has been minimized, the constant k in equation (2) may be determined by generating a known value of $V_T$ and determining the value of $V_T'$ output. The known value of $V_T$ may be conveniently generated, typically using the voltage-temperature relations referred to above, by applying a known temperature to the distal end of the probe. Such a known temperature may be applied while the probe is not being used for a medical procedure. Alternatively or additionally the determination of k may be performed while the probe is being used during a medical procedure, in which case the body temperature of patient 28 may be assumed to be the known temperature. Typically, although not necessarily, the determination of k is performed during the calibration operation described above.

Typically, processor 52 stores the value of k, values of parameters used to adjust elements 84 and 86, as well as values of other parameters for operation of system 20 such as those used to set the gain of amplifier 96, in memory 54.

Referring back to FIG. 3, generator 70 is assumed to provide two outputs, a first for power amplifier 72, and a second for local oscillator input terminal L of mixer 82, so that the amplifier and the terminal operate at the same radiofrequency. It will be understood that other methods may be implemented in circuit 58 to achieve the common radiofrequency required. For example, a local oscillator supplying the mixer may be locked by a phase-locked loop (PLL) to a frequency generator for the RF ablation energy. All such methods are assumed to be comprised within the scope of the present invention.

The embodiments described above have used, by way of example, an ablation electrode that receives an RF voltage, and a thermocouple that has impressed upon it a leakage component of the RF voltage by virtue of the electrode and thermocouple having a common conductor. As explained above, the low-frequency voltage generated by the thermocouple is recovered and detected by cancelling the leakage component of the RF voltage in a mixer. It will be understood that this principle of cancellation may be applied to other elements that may be comprised in probe 22.

As a first example, a foil strain gauge may replace thermocouple 38, one of the conductors to the strain gauge being used as a common conductor that is also configured to convey the RF voltage to the ablation electrode. As a second example, the ablation electrode may also be configured to receive ECG (electrocardiogram) signals on the conductor conveying the RF voltage to the ablation electrode. In both examples, a leakage component of the RF voltage may be cancelled in a mixer, and the recovered low-frequency strain gauge voltage or ECG signal detected. Other examples of elements that may be incorporated in probe 22, that use the principle of cancellation described herein, will be apparent to those having ordinary skill in the art, and are assumed to be comprised within the scope of the present invention.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Medical apparatus, comprising: a probe comprising an ablation electrode; a first conductor connected to the ablation electrode and configured to convey ablation energy thereto; a second conductor connected at a junction to the first conductor so as to form a thermocouple at the junction; a radiofrequency generator coupled to the first conductor and configured to generate the ablation energy; a mixer coupled to the first and second conductors so as to receive a voltage therefrom and to output a resultant output generated by mixing the voltage from the first and second conductors; and a processor coupled to the first and second conductors so as to measure a temperature of tissue to which the ablation energy is applied.

2. The apparatus according to claim 1, wherein the mixer is configured to receive radiofrequency energy from the radiofrequency generator as a local oscillation.

3. The apparatus according to claim 1, wherein the resultant output of the mixer is a radiofrequency signal having a frequency determined by the radiofrequency generator.

4. The apparatus according to claim 3, wherein an amplitude of the resultant radiofrequency signal output by the mixer is a function of the temperature of the tissue.

5. The apparatus according to claim 3, wherein an amplitude of the resultant radiofrequency signal output by the mixer is a function of the voltage from the first and second conductors.

6. A method for providing a medical apparatus, comprising: providing a probe comprising an ablation electrode; connecting a first conductor to the ablation electrode; configuring the first conductor to convey ablation energy to the ablation electrode; connecting a second conductor at a junction to the first conductor so as to form a thermocouple at the junction; coupling a radiofrequency generator to the first conductor and configuring the radiofrequency generator to generate the ablation energy; coupling a mixer to the first and second conductors so as to receive a voltage therefrom and to output a resultant output generated by mixing the voltage from the first and second conductors; and coupling a processor to the first and second conductors so as to measure a temperature of tissue to which the ablation energy is applied.

7. The method according to claim 6, wherein the mixer is configured to receive radiofrequency energy from the radiofrequency generator as a local oscillation.

8. The method according to claim 6, wherein the resultant output of the mixer is a radiofrequency signal having a frequency determined by the radiofrequency generator.

9. The method according to claim 6, wherein an amplitude of the resultant radiofrequency signal output by the mixer is a function of the temperature of the tissue.

* * * * *